US008657806B2

(12) United States Patent
Eckstein et al.

(10) Patent No.: US 8,657,806 B2
(45) Date of Patent: *Feb. 25, 2014

(54) DEVICE SUITABLE FOR CARRYING ON THE BODY OF A USER TO GENERATE VACUUM FOR MEDICAL APPLICATIONS

(75) Inventors: Axel Eckstein, Heidenheim (DE); Juergen Hofstetter, Heidenheim (DE); Mario Moeller, Loeffingen (DE); Andreas Heer, Stuehlingen (DE); Simon Wegner, Titisee-Neustadt (DE)

(73) Assignees: Paul Hartmann AG, Heidenheim (DE); ATMOS Medizin Technik GmbH & Co. KG, Lenzkirch (DE)

( * ) Notice: Subject to any disclaimer, the term of this patent is extended or adjusted under 35 U.S.C. 154(b) by 205 days.

This patent is subject to a terminal disclaimer.

(21) Appl. No.: 12/805,489

(22) Filed: Aug. 3, 2010

(65) Prior Publication Data

US 2011/0040288 A1 Feb. 17, 2011

Related U.S. Application Data

(60) Provisional application No. 61/295,186, filed on Jan. 15, 2010.

(30) Foreign Application Priority Data

Aug. 12, 2009 (DE) .......................... 10 2009 038 131

(51) Int. Cl.
*A61M 27/00* (2006.01)
*A61M 1/00* (2006.01)
*A61M 3/00* (2006.01)
*A47L 5/00* (2006.01)

(52) U.S. Cl.
USPC ............... 604/543; 604/541; 604/43; 604/35; 604/313; 604/319; 604/327; 604/318; 15/325

(58) Field of Classification Search
USPC ............. 604/541, 543, 43, 35, 313, 319, 327, 604/318; 15/352
See application file for complete search history.

(56) References Cited

U.S. PATENT DOCUMENTS 4,569,674 A * 2/1986 Phillips et al. ................ 604/119
5,776,119 A * 7/1998 Bilbo et al. ................... 604/317

(Continued)

OTHER PUBLICATIONS

"portable." Collins English Dictionary—Complete and Unabridged. HarperCollins Publishers. May 15, 2012. <http://thefreedictionary.com/portable>.*

*Primary Examiner* — Jacqueline Stephens
*Assistant Examiner* — Andrew J Mensh
(74) *Attorney, Agent, or Firm* — Paul Vincent

(57) ABSTRACT

A device for carrying on the body of a user to generate a vacuum for medical applications, having a vacuum-producing device and a disposable vessel, with a suction tube connection leading to Ihe body, wherein the vacuum-producing device is disposed in a first housing part of the device and the vessel forms a second housing part of the device, and the housing parts are separably fixed one against the other, the device having body fastening means. The housing pans can be separably fixed to each other by a positive-action locking mechanisms and the locking mechanism having a manually operable operating element. The first and/or second housing part is constituted for manual gripping so that the device or the first or second housing part can be gripped and separated from the other housing part, and the manually operable operating element is provided in the region of the manual gripping.

33 Claims, 10 Drawing Sheets

(56) References Cited

U.S. PATENT DOCUMENTS

| | | | |
|---|---|---|---|
| 6,142,982 A * | 11/2000 | Hunt et al. | 604/313 |
| 6,383,266 B1 * | 5/2002 | Conrad et al. | 96/57 |
| 6,695,823 B1 * | 2/2004 | Lina et al. | 604/304 |
| 6,836,931 B2 * | 1/2005 | Bone | 15/352 |
| 8,007,481 B2 * | 8/2011 | Schuessler et al. | 604/313 |
| 8,048,046 B2 * | 11/2011 | Hudspeth et al. | 604/313 |
| 2002/0108208 A1 * | 8/2002 | Hamada et al. | 15/352 |
| 2003/0040687 A1 * | 2/2003 | Boynton et al. | 601/6 |
| 2006/0074362 A1 * | 4/2006 | Rousso et al. | 601/152 |
| 2007/0179460 A1 | 8/2007 | Adahan | |
| 2007/0251048 A1 * | 11/2007 | Choi | 15/329 |
| 2008/0004549 A1 | 1/2008 | Anderson | |
| 2008/0082059 A1 * | 4/2008 | Fink et al. | 604/305 |
| 2009/0043268 A1 * | 2/2009 | Eddy et al. | 604/290 |
| 2009/0079701 A1 | 3/2009 | Grosskopf | |
| 2009/0157019 A1 | 6/2009 | Koch | |
| 2009/0163882 A1 * | 6/2009 | Koch et al. | 604/319 |
| 2009/0240218 A1 * | 9/2009 | Braga et al. | 604/313 |
| 2010/0185164 A1 | 7/2010 | Hartwell | |
| 2010/0185165 A1 * | 7/2010 | Middleton et al. | 604/319 |
| 2010/0187065 A1 | 7/2010 | Pidgeon | |

* cited by examiner

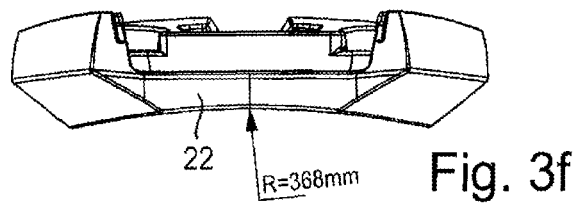
Fig. 3f
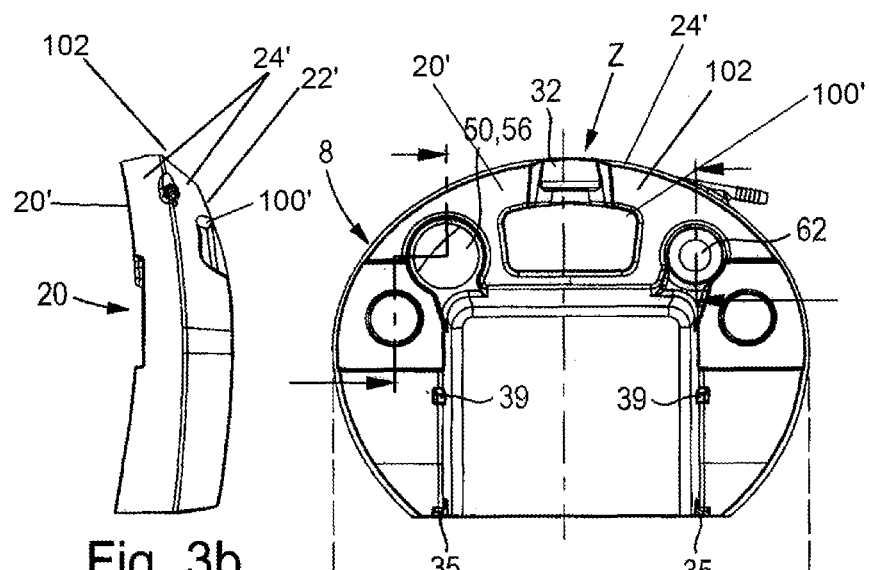
Fig. 3b
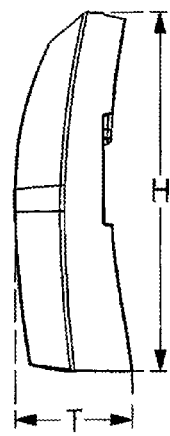
Fig. 3c
Fig. 3a
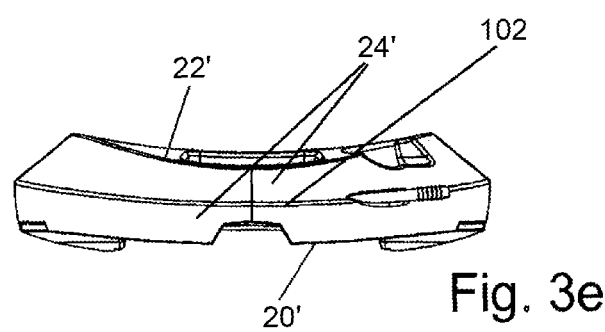
Fig. 3e

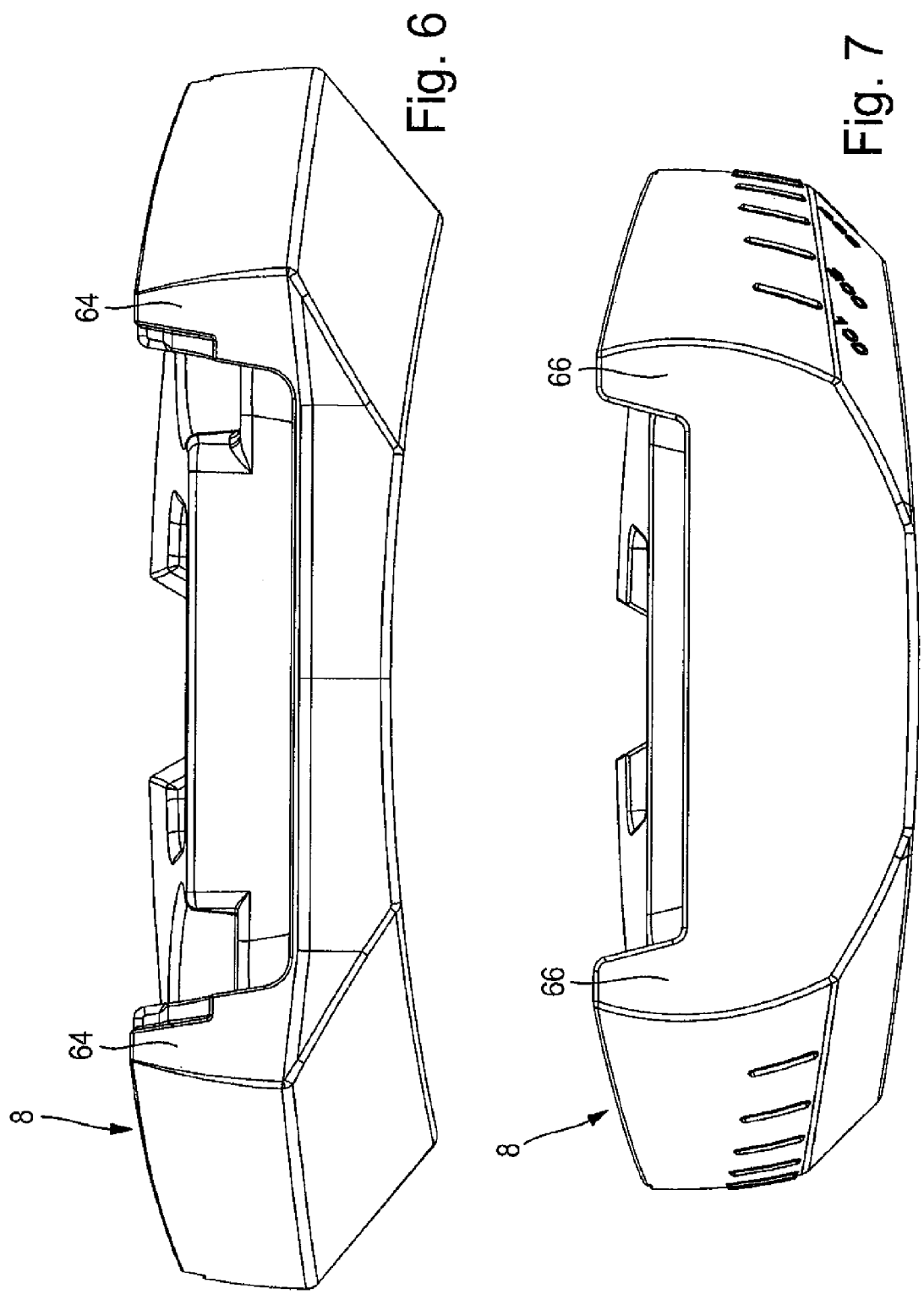

DEVICE SUITABLE FOR CARRYING ON THE BODY OF A USER TO GENERATE VACUUM FOR MEDICAL APPLICATIONS

This application claims benefit of provisional application 61/295,186 filed Jan. 15, 2010 as well as Paris Convention priority of DE 10 2009 038 131.7 filed Aug. 12, 2009, the entire disclosures of which are hereby incorporated by reference.

BACKGROUND OF THE INVENTION

The invention concerns a device suitable for carrying on the body of a user to generate vacuum for medical applications, in particular, for the vacuum therapy of wounds on the bodies of humans or animals, with a vacuum-producing facility and a single-use vessel to be discarded after use for holding body fluids, in particular, wound exudates suctioned out of a wound, and with a connector for a suction tube carried on the body for this purpose, wherein the vacuum-producing facility is disposed in or on a first housing part of the device and the vessel constitutes a second housing part of the device or is disposed in or on the second housing part, and the housing parts can be separably fixed to each other, wherein the device has fastening means enabling it to be carried on and moved with the body of the user.

Such devices for the vacuum therapy of wounds have already been disclosed by multiple sources, in particular, by US 2004/0073151 A1, WO 2009/047524 A2, WO 2007/030599 A2, and EP 1 905 465 A1.

In such devices for the vacuum therapy of wounds, a vacuum-producing device communicates with the wound or the region of the wound through a suction tube, wherein a cover material that is impermeable to air is provided for air-tight closure of the wound and the region of the wound, so that a vacuum can be established in the wound space and liquids from the wound space can be suctioned into the aforementioned vessel.

The term vacuum in connection with this invention refers to a lower air pressure than ambient air pressure (atmospheric pressure), in particular inside the wound dressing. The cover material of a wound dressing for air-tight closure of a wound space must therefore be constituted such that it can withstand the established pressure difference so that the vacuum in the wound space can be initially produced and then maintained. In vacuum therapy for wound treatment, the vacuum is quantitatively expressed as the pressure difference between the ambient air pressure and the air pressure applied underneath the cover material. In vacuum therapy, this pressure difference is typically no more than 250 mm Hg (mm of mercury) (1 mm Hg=1 Torr.=133.322 Pa). This vacuum range not exceeding 250 mm Hg has proven advantageous for wound healing. A preferred vacuum range is between 10 and 150 mm Hg.

The vacuum applied to the wound using the device can, in typical vacuum therapy, either be kept essentially constant over time or it can vary over time, in particular, cyclically, which can be implemented using an appropriately constituted and programmed control device on the device producing the vacuum, in particular, in dependence on further parameters.

To apply the vacuum and preferably also to suction away body fluids, a preferably flexible suction tube, for example, in the form of a drainage tube, is provided that communicates at one end through a port in the region of the wound cover material with the wound environment or the wound space and at the other end with the vessel stated above for receiving body fluids or with the device producing the vacuum.

In addition to the vacuum therapy of wounds, other applications of the device described here are conceivable for providing a vacuum for medical applications, in particular, the removal by suction of any body fluids in medical incontinent care, the care of stoma patients, or for the removal by suction of wound exudates, possibly, using rinsing liquids, and also without the application of a vacuum over considerable periods.

The object of this invention is to improve a device of the type described above so that it can be handled in a still more user-friendly way.

SUMMARY OF THE INVENTION

This object is inventively solved in a device of the type stated in that the housing parts can be separably fixed to each other by snap-in, latching, or other positive-action locking or back-gripping means and that the locking or back-gripping means can be moved into a release direction by a manually operable operating element and that the first and/or second housing part is constituted for manual gripping so that the device or the first or second housing part can be gripped in this manner and can be separated from the other housing part, and that the manually operable operating element for the locking or back-gripping means is provided in the region of the manual gripping so that a user or a caregiver can, with only one hand, release the locking or back-gripping means while gripping the one housing part and release and remove it from the other housing part.

In this way, according to the invention, single-hand operation of the device as a whole is possible, enabling the user to hold, lift, or handle the device as a whole or the relevant housing part. This permits one-handed access to the second housing part and one-handed release of the second housing part after use, that is, when filled with body fluids, from the device and one-handed disposal therefore in a disposal container, in particular, for septic waste. The contaminated second housing part then no longer needs to be set down but can be unlocked, removed from the first housing part, and disposed of in a single action, which proves especially advantageous. The second housing part is therefore preferably constituted for manual intervention.

For the purpose stated above, any gripping means could be provided on the first and/or second housing part, that is, for example, a web that can be gripped, gripped around or gripped under with the fingers. In a preferred embodiment of the invention, the first and/or second housing part has as gripping means, a gripping cavity or gripping recess that can also be constituted in a further embodiment of the invention as passing right through the first and/or second housing part, that is, as a passage opening. In this way, the user can grip the housing part in accordance with the anatomy of the relaxed hand while operating the operating element with his or her thumb.

In a further embodiment of the invention, it proves advantageous if a gripping means, in particular, a gripping cavity or a gripping recess is provided in an upper region of the first and/or second housing part inclined away from the body, in particular, on the side of the second housing part facing the body. In this way, the user is easily able to grip the device with one hand, even during mobile operation, and, with the other hand, release a belt-like fastening means, to be described below.

According to one embodiment of the invention, it proves advantageous that the locking or back-gripping means projects from the separation plane of one of the housing parts and can be deflected transversely with respect to the joining direction of the housing parts during joining of the housing parts and can be put into a back-gripping position.

The manually operable operating element can basically be disposed on the device that is near enough for manual access to a gripping means on the housing parts. However, it proves advantageous if it is provided on the top side of the device and, in particular, as a button that can be pressed in. In this way, it is possible to set down the device on a preferably horizontal surface and then to operate the operating element successfully without the device sliding away to the side.

In a further embodiment of the invention, it proves advantageous if the first housing part faces away from the body when the device is carried on the body of the user (mobile operation) and the second housing part faces the body. It also proves advantageous if both housing parts are essentially constituted disk-shaped and lie one against the other in an essentially vertically oriented separation plane.

For the purpose of this invention, the disk shape of the two housing parts means that the housing parts, when they are set down as intended during stationary operation with their standing side on a horizontal support surface, each have a width and height that is larger than their depth when viewed horizontally. Therefore, when they are separably fixed together, the housing parts rest one against the other with the side that is in the disk plane. The separation plane stated above does not necessarily mean that the housing parts lie against one other on an exact flat surface. Rather protrusions advantageously acting as centering means or similar shaped elements can be provided on the housing parts in preferably complementary shapes. According to the invention, the two housing parts are therefore not inserted into one another nor stacked upon one another but they lie side by side and one against the other on the aforementioned essentially vertically oriented separation plane when the device is set down as intended with its standing side on a horizontal surface or is carried on the body of a person standing upright.

Because, in mobile operation of the device, the vessel forming the second housing part or disposed in or on the second housing part together with the second housing part is oriented facing toward the body and the first housing part accommodating the vacuum-producing facility is facing away from the body, it is possible to cover the second housing part by means of the first housing part. In this way, the second housing part or the vessel could also be constituted to be transparent without permitting third parties to see directly in. Moreover, the configuration of the second housing part in the region of the body affords greater design options for adaptation to the body than would be the case for the first housing part accommodating the vacuum-producing facility. Furthermore, due to the configuration of the first housing part facing away from the body, access can be provided to the operating elements for the vacuum-producing facility and its control on the visible side of the device. In this way, access is also possible by the user to the device itself by disposing the operating components and possibly also display components facing away from the body and preferably visible from above.

In a further embodiment of the invention, it has proven especially advantageous if the second housing part is constituted concave toward the user on its side facing the body of the user in at least one preferably horizontal plane so that it can be applied ergonomically to the body. The device can be worn, for example, in this way in the hip region in a manner that is comfortable for the user. In this case, the aforementioned plane extends essentially horizontally in the case of a standing user/patient and the intersecting line of this plane with the side of the second housing part that faces the body then extends concavely. For this purpose, a radius of curvature in at least some sections of 300 to 500 mm, in particular of 300 to 400 mm, has proven advantageous.

It can further prove advantageous if the second housing part is concave at least in regions in a horizontal and in a vertical plane on its side facing the body of the user. This can, for example, also make it easier to position the device in the hip region of a user. For a concave shape in a vertical plane, a radius of curvature, at least in sections, of 500 to 900 mm, in particular, of 600 to 800 mm, in particular, of 700 to 800 mm proves advantageous.

However, an embodiment is also conceivable, for example, in which the second housing part is concave on its side facing the body in a horizontal plane and convex in sections in its vertical plane so that overall it has the shape of a saddle.

Irrespective of this, it can prove advantageous if the second housing part is beveled away from the body of the user toward the first housing part on its side facing the body of the user in a region facing away from the standing side of the device (that is, the top). This bevel can advantageously be ergonomically rounded although this is by no means essential. In this way, the device lies against the body of the user with a slightly smaller surface of the second housing part, which enables the user to bend his or her body over the device. It similarly can prove advantageous if the second housing part is beveled in the transition to the side walls of the second housing part or to the side walls of the first housing part on its side facing the body of the user.

For user-friendly joining of the first and the second housing parts, it proves advantageous if the first and the second housing parts have centering means on their sides facing each other and if the housing parts can be joined together essentially transversely with respect to a separation plane. These centering means can be constituted in any way, for example, by pin-shaped or cone-shaped elements or by protruding and recessed housing regions that can, in particular, also be constituted in the shape of a block or box and preferably interact in a complementary way and with appropriate lead-in bevels to ensure centering. These centering means or the contacting sides of the housing parts are preferably constituted in such a way that they can only be joined in the correct manner.

To join the housing parts, it proves advantageous if the one housing part can be placed on a contact surface of the other housing part from above with a slightly upward inclination with respect to the vertical and can then be pivoted essentially transversely with respect to the separation plane into contact with the other housing part.

It proves essentially advantageous if, when joining the first and the second housing parts, vacuum communication is simultaneously established between the vessel and the vacuum-producing facility so that the joining operation is user-friendly overall and the user does not come into contact with body fluids. Analogously, this idea is even more important when separating the housing parts after use.

To ensure the device stands firmly during stationary operation or when the device is temporarily set down on a preferably flat surface, it proves advantageous if a center of gravity of the device (while the vessel is still unused) is in the lower half of the device, that is, below an imaginary horizontal central plane half way up the device.

To achieve this, it proves advantageous if the ratio of the standing surface of the device to its height is 4.0-6.0 cm$^2$/cm, in particular, 4.5-5.5 cm$^2$/cm. The standing surface of the device can, for example, be approximately 81 cm$^2$ and its height approximately 16 cm.

It is conceivable and advantageous for many applications if the standing surface of the device is constituted by both housing parts when its two housing parts are joined together.

In a further embodiment of the invention, however, it has proven sufficient if the standing surface of the device is only formed by the first housing part. For this purpose, it proves advantageous if the first housing part forms a region projecting into a form recess of the first housing part that forms part of the standing surface. In this way, it is ensured after the first housing part has been removed from the second housing part that the vacuum-producing facility and its control components continue to stand as firmly as they did before.

According to a further inventive idea, it is proposed that the device be constituted in such a way that the first housing part covers the second housing part, when viewed from the front onto a visible side of the first housing part facing away from the body, preferably completely or at least covering 90% of the visible surface in this viewing direction. This further enables the second housing part to be constituted inexpensively because it is only visible to the user or to third parties to a small extent in the region of its side surfaces when the device is worn on the body of the user. The vessel therefore no longer has to be "concealed" in carrying bags.

According to an especially important inventive idea, it is proposed that the device comprise a plurality of second housing parts each with a vessel as a sort of collective item that are optionally connectable with the first housing part to form the device, wherein the second housing parts and their vessels are of different sizes, in particular, in the depth direction, that is, toward the user. In this way, different holding capacities can be provided by different housing parts and their vessels. Housing parts can be provided for this that are suitable for mobile operation and others that are more suitable for stationary operation, that is, in particular, those with a larger volume so that the vessels require less frequent replacement when receiving liquids.

To prevent contamination and blockage of the vacuum-producing facility, it proves advantageous if a filtering means is provided between the vessel and the vacuum-producing facility that can be discarded together with the vessel after use as a disposable item.

It further proves advantageous if a filling level indicator is provided for the vessel. This filling level indicator can, for example, be implemented by a sufficiently transparent housing wall of the second housing part or it can be constituted in any other way, in particular, using electronic sensors and display means. A monitoring facility also proves advantageous that outputs an alarm depending on the filling level reached in the vessel. The vessel of the second housing part can contain a superabsorbent medium to bind the suctioned-in liquid and to prevent the liquid from sloshing.

It has already been pointed out that the inventive embodiment of the device advantageously allows operating elements and display elements for the vacuum-producing facility to be provided on a visible side of the first housing part facing away from the body. The operating elements are advantageously constituted in the form of a touchscreen.

According to an independent inventive idea, it proves advantageous if an inclination sensor is provided on the first housing part, which causes the display on a display element to rotate through preferably 180° at a defined inclination of the first housing part with respect to the vertical by means of a control facility so that it can be read by the user from above. From the normal vertical position of the device, when it is in stationary operation, for example, or when it is worn in mobile operation by a user standing upright, the user only needs to incline the device by a defined inclination, in particular, through 45°, in particular, through 40°, in particular, through 30° for the display on the display element to rotate so that the user can read the display from above.

According to a further inventive idea of essential importance, it proves advantageous if the entire visible side of the first housing part facing away from the body is essentially constituted or overlapped by a large-surface cover to avoid dirt-trapping joints in the region of the operating elements.

It further proves advantageous if, on the first housing part, an interface for data exchange, in particular, a USB interface, is provided, in particular, in the separation plane with the second housing, and is thus covered and, in particular, protected against soiling by the second housing part. In this way, program control information can be transferred to an electronic control facility of the device.

The fastening means already mentioned for fastening the device on the body of the user for mobile operation of the device advantageously comprise a flexible strip-shaped or belt-shaped section or a plurality of such sections that can be separably fastened on opposite sides of the first and/or second housing part, that is, can be released from the housing parts for stationary operation of the device. The fastening means can also be bows or straps placed on the outer side of the housing parts to which further fastening means are releasably joined, for example, belt sections, carrying straps, or the like.

The fastening means are advantageously releasably disposed between the housing parts lying one against the other. They can, in particular, be plugged into a plug slot between the mutually contacting housing parts or can be releasably coupled on bows, straps, or similar provided on the outer side of the housing parts.

The preferably flexible fastening means are placed around the circumference of the body in the manner of a belt preferably in the hip region or in any case around the thigh, upper arm, or thorax and thus hold the device on the body. Fastening means can especially preferably be connected to and released again from the first and/or second housing part of the device in the manner of a quick-release lock. The fastening means can, at their free ends, have quick-release locking means that can be plugged into the housing parts, in particular, with spring-action back-grip means, or bows that can be plugged in or otherwise fastened for the fixture of flexible fastening means. In a preferred embodiment, the fastening means are releasably disposed between the first and the second housing part, that is, in the separation plane between the housing parts. An embodiment is conceivable and advantageous in which the fastening means can be removed by separating the housing parts. Or an embodiment is conceivable and advantageous in which release of the fastening means is possible irrespective of whether the housing parts have been separated. An additional shoulder belt or strap can be provided that can be used alternatively or additionally to a hip belt. For example, it can be releasably applied by means of a carabiner lock or of any quick-release lock on a bow or on a strap on the housing parts.

It further proves advantageous if the housing parts in the joined condition of the device do not have any back-grippable components on the outer side, with the exception of the connection for the suction tube or a measuring or rinsing duct and any grip cavity or grip recess.

Further characteristics, details, and advantages of the invention can be derived from the appended claims and from the drawings and the following description of preferred embodiments of the inventive device. For the characteristics of the claims, protection is claimed separately and in any combination, irrespective of dependency of the claims. The drawing shows:

BRIEF DESCRIPTION OF THE DRAWING

FIGS. 3a to i various views of a second housing part of the device according to FIG. 1, constituting a vessel to receive body fluids;

FIGS. 6, 7 a view of the second housing part of the devices according to FIGS. 1 and 4 from below to illustrate the different standing surfaces of these second housing parts.

DESCRIPTION OF THE PREFERRED EMBODIMENT

Figure 1A:
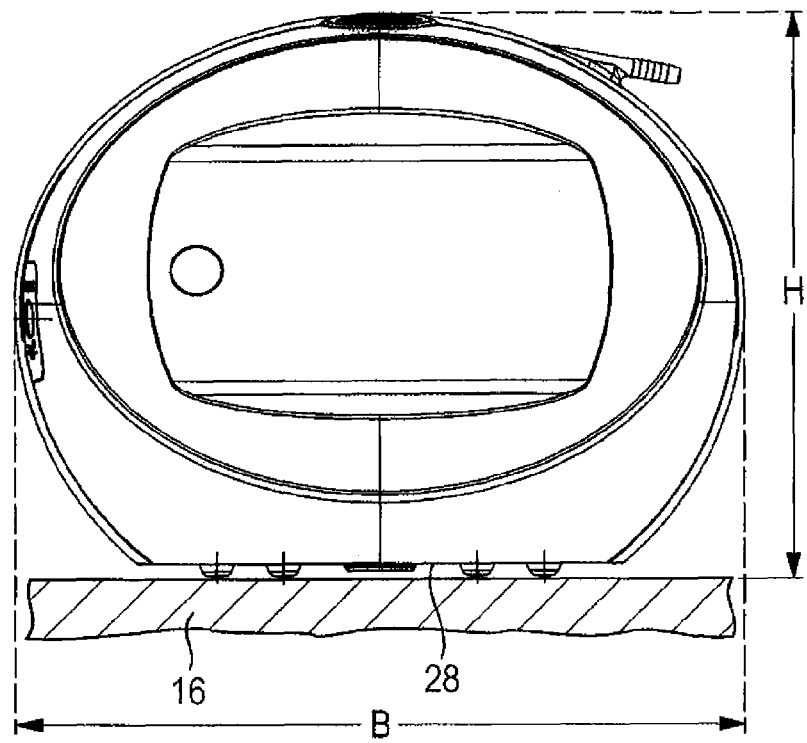
FIGS. 1a to e different views of a preferred embodiment of the inventive device for carrying on the body to generate a vacuum for medical applications.
Figure 1B:
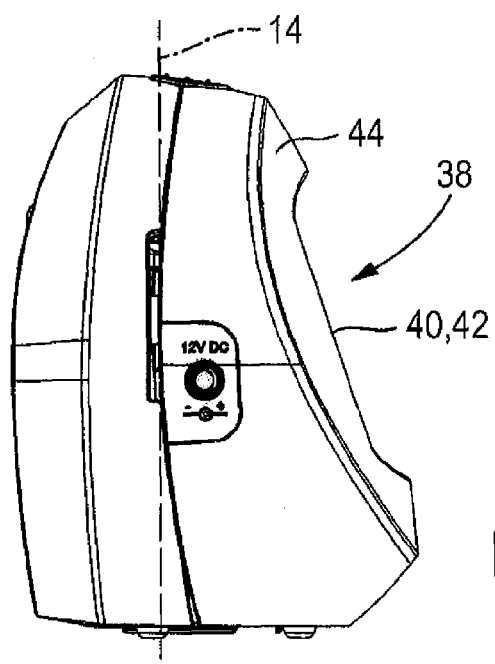

FIGS. 1a to e show a first embodiment of an inventive portable device 2 for the provision of the vacuum for medical applications. The device comprises a first housing part 4 in which a vacuum-producing device in the form of an air pump and electrical and electronic control components for the device are accommodated completely, including batteries or preferably rechargeable batteries. A recharging connection for the batteries is designated by reference symbol 6. Moreover, the device 2 comprises a second housing part 8 that preferably is also a vessel 10 for receiving body fluids, in particular, for receiving wound exudates suctioned away from a wound. The entire second housing part 8 is preferably constituted as a disposable single-use item. In its upper region, a connection gland 12 for a suction tube, not depicted, is provided that can, for example, lead to a wound dressing that closes the wound pressure-tight when the device 2 is used in the vacuum therapy of wounds and there it can, for example, communicate with the wound space through a port to apply and maintain a vacuum to the wound space and to suction away wound exudates into the vessel 10. For this purpose, the vessel 10 communicates with the vacuum-producing device. Further, a connection 13 is shown for an optional measuring or rinsing duct that is guided to the wound, like the suction tube. This connection passes through the second housing part 8 and exits into the first housing part 4, from where, for example, air as the rinsing medium can be applied to the measuring or rinsing duct and/or pressure in this measuring or rinsing duct can be detected and evaluated.

Figure 1C:
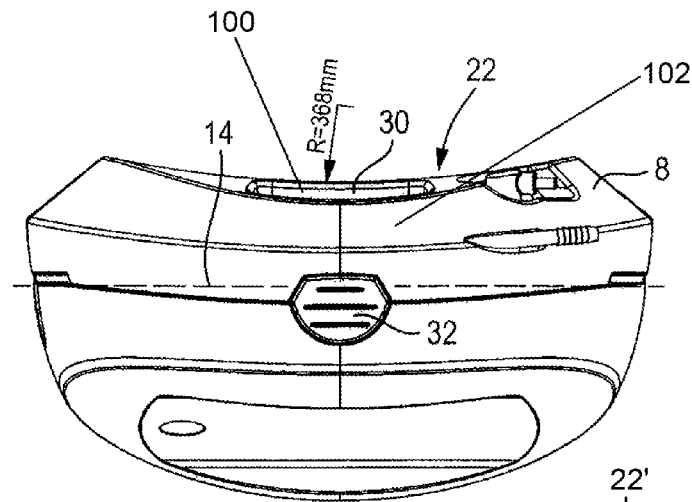
Figure 1D:
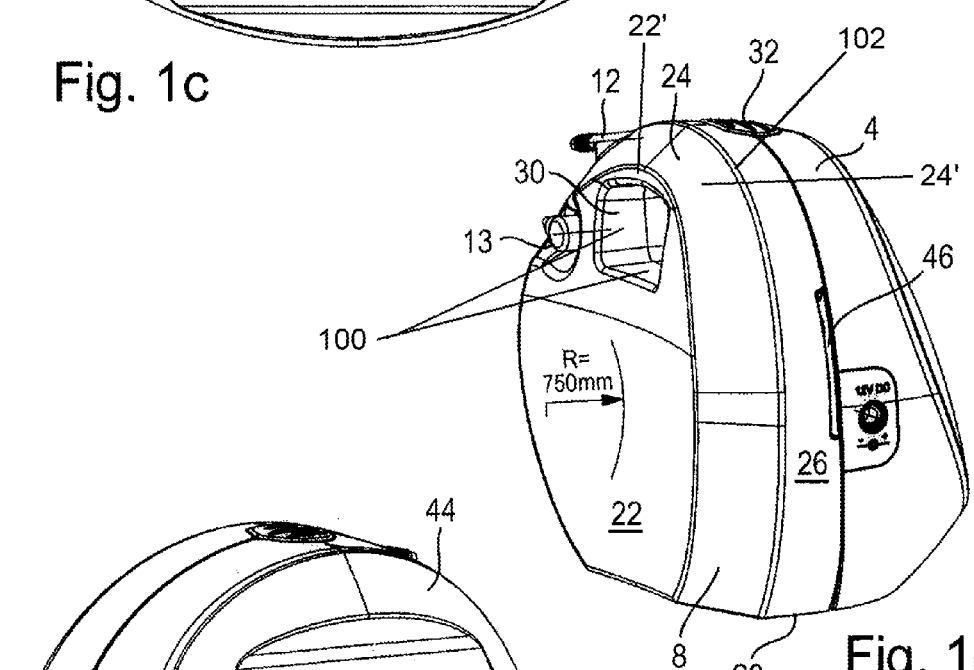
Figure 1E:
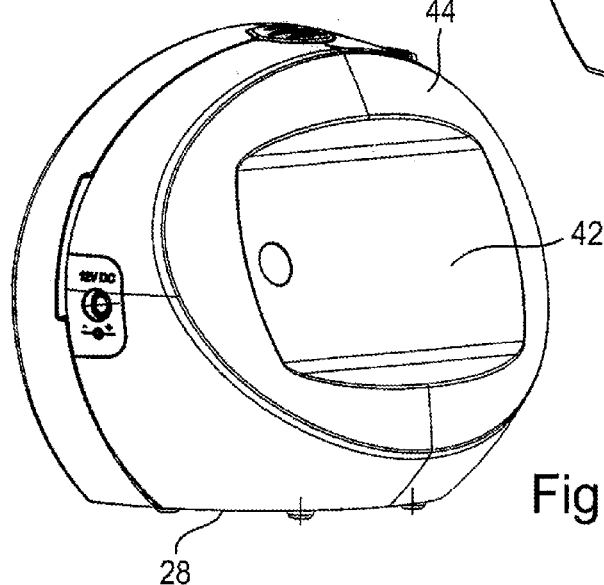

According to the invention, the housing parts 4 and 8 lie one against the other on an essentially vertical separation plane 14 that is indicated in the various figures. When the device 2 is set down on an even horizontal surface 16, as shown in FIG. 1a, the separation plane 14 is oriented essentially vertically. This means that the two housing parts 4, 8 are not inserted one into the other nor stacked one upon the other, but that they remain side by side when the device 2 is joined as intended. As can be seen directly from FIGS. 2a to e, which show the first housing part 4 in various views, the term separation plane 14 is not to be understood as a geometrically flat surface. It is immediately apparent that the side 18 of the first housing part 4 facing the second housing part 8 is not flat but formed with a multiplicity of elements projecting toward the second housing part 8. The side 20 of the second housing part 8 facing the first housing part 4 is constituted essentially complementarily to the shape of the side 18 of the first housing part 4 so that the two housing parts 4, 8 can only be joined and fastened together in the correct manner. The two housing parts 4, 8 are constituted disk-shaped overall, that is, their width B in the horizontal direction and their height H in the vertical direction are larger than their depth T in the horizontal direction and perpendicular to the extent of the width. In this way, it is possible for the device 2 to be constituted and dimensioned overall such that it can be comfortably worn on the body of the user. According to the invention, the device 2 is constituted such that the vessel parts 4, 8 disposed side by side can be positioned on the body in such a way that the second vessel part 8 is facing the body, that is, between the body and the first housing part 4 and the first housing part 4 is facing away from the body, that is, it essentially forms the visible side of the device 2. For that reason, the side 22 of the second housing part 8 facing the body of the user is rounded. As can be seen from FIGS. 1c, 1d, 3f, 3e, the side 22 facing the body is formed concavely, seen in cross-section in a horizontal plane, and comprises, for example, in the case shown, a radius of curvature R in some sections of, for example, 368 mm (FIG. 1c, 3f). Additionally, the side 22 facing the body is also constituted concavely, seen in cross-section in a vertical plane, and has a radius of curvature R of, for example, 750 mm (FIG. 1d). In this way, the device 2 can be ergonomically disposed and worn in the hip region of a user.

It can also be seen that the second housing part 8 on its side 22 facing the body in an upper region and also on the side comprises a bevel 24 away from the body of the user toward the first housing part 4 or toward the side walls 26 and a circumferential facing end of the disk shape of the second housing part 8. The bevel 24, in the example shown here, runs round the full circumference; it extends from the standing side 28 from bottom to top, runs in an arc from there to the other side and then back down to the standing side 28.

It can also be seen from FIGS. 1d and 3 that, on the side 22 of the second housing part 8 facing the body, a grip recess 30 is formed in the shape of an opening extending right through the second housing part 8, and this in an upper region of the second housing part 8 slightly inclined away from the body. In this way, the device 2, or only its second housing part 8, can be gripped and handled with one hand.

Figure 2A:
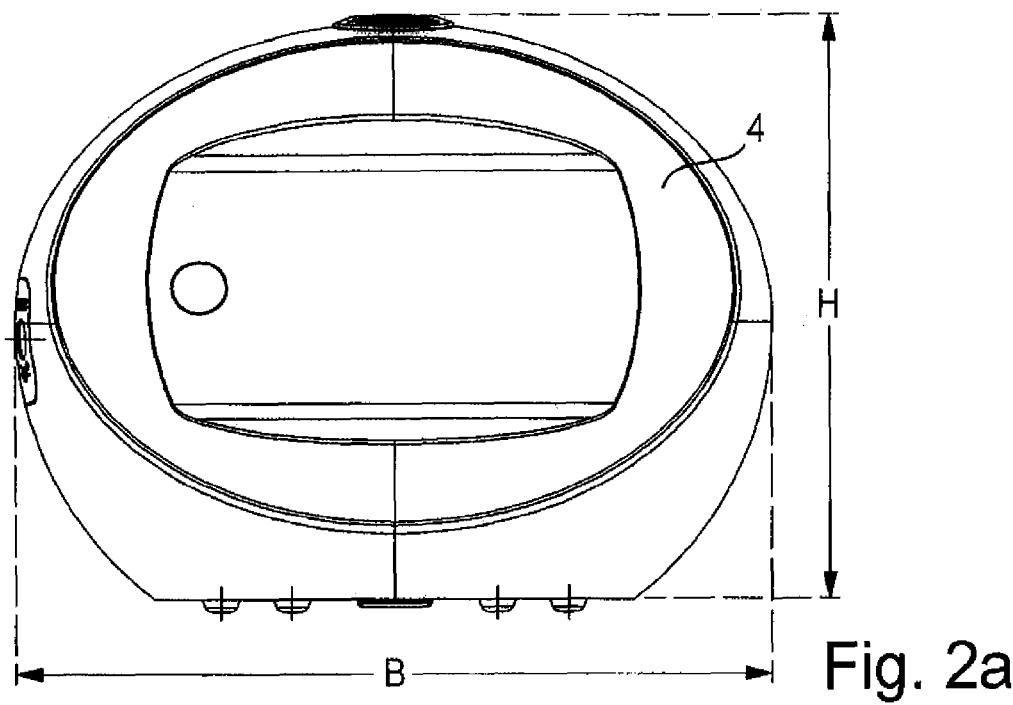
FIGS. 2a to e various views of a first housing part of the device according to FIG. 1, comprising a vacuum-producing device and control components.
Figure 2B:
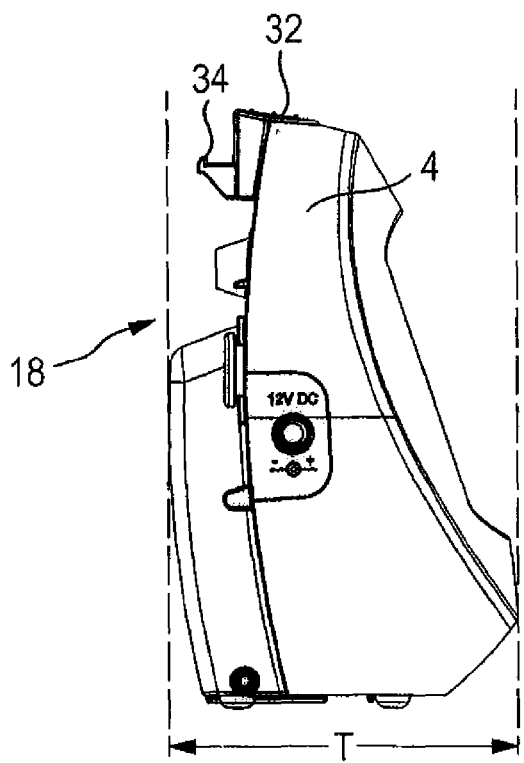
Figure 2C:
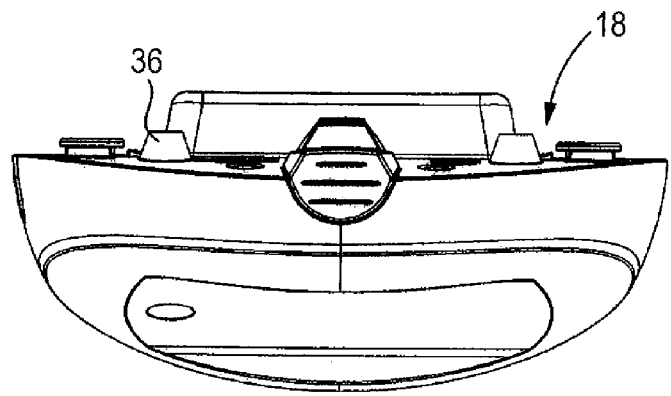
Figure 2D:
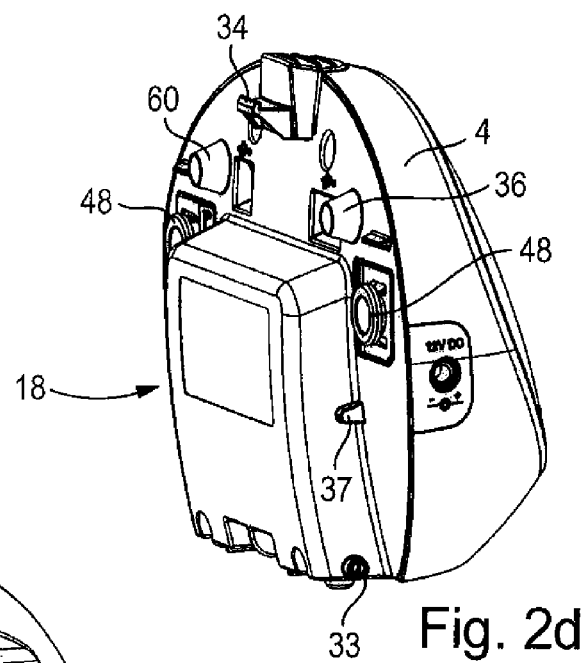
Figure 2E:
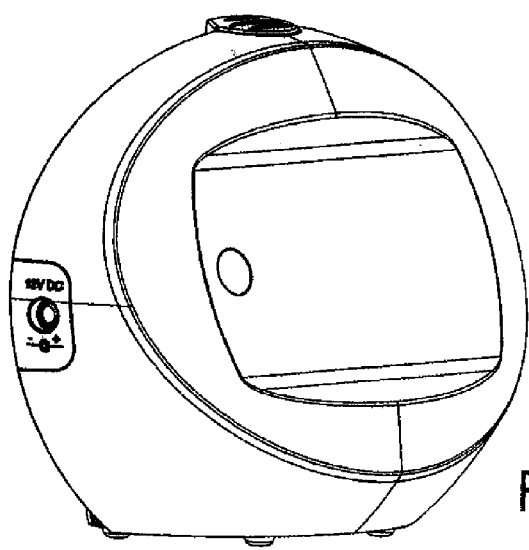
Figure 3D:
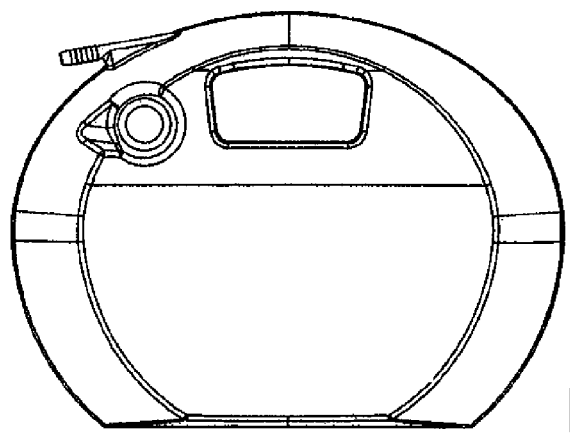
Figure 3G:
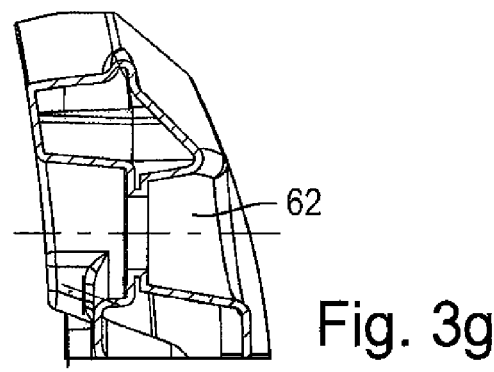
Figure 3H:
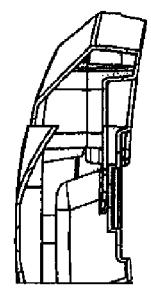
Figure 3I:
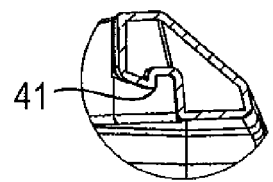
Figure 4A:
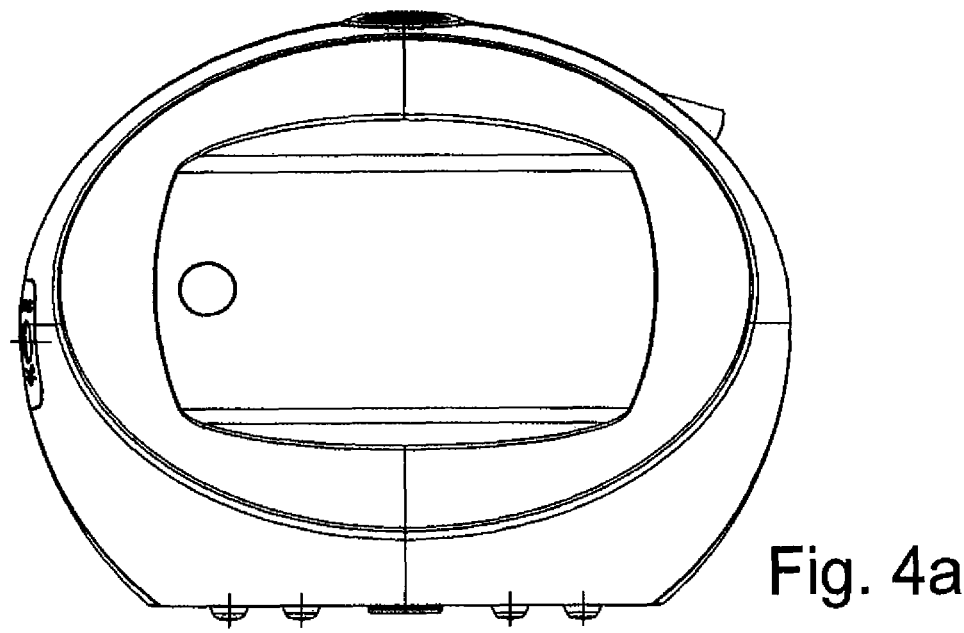
FIGS. 4a to e views corresponding to FIGS. 1a to e of a further embodiment of the inventive device, wherein the second housing part is dimensioned larger than in the device according to FIGS. 1a to e.
Figure 4B:
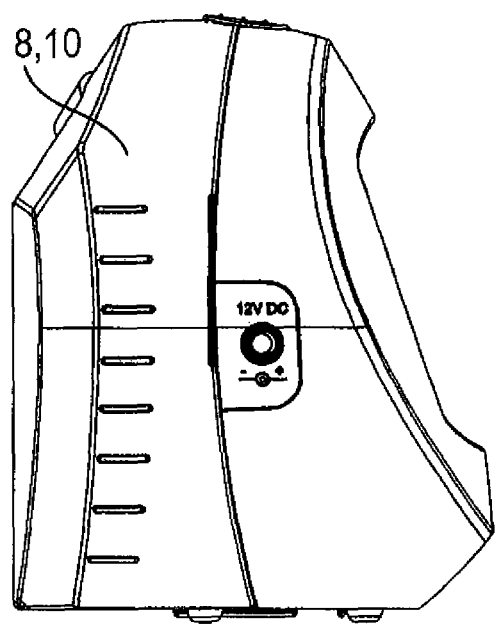
Figure 4C:
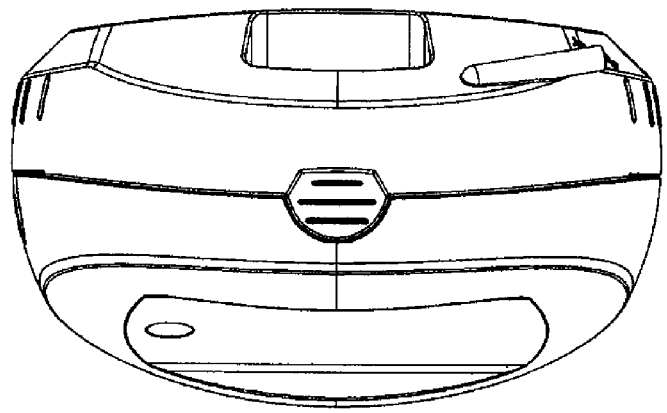
Figure 4D:
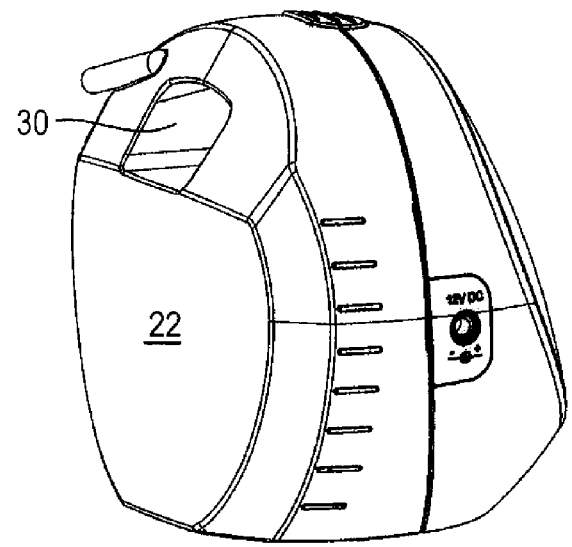
Figure 4E:
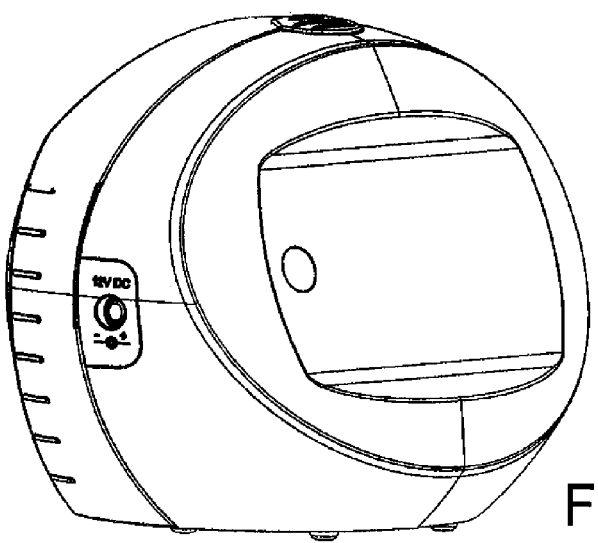

In the preferred embodiment shown, a manually operable element 32 is provided in this grip recess 30 on the upper side of the device 2, for example, in the form of a pushbutton that acts on the locking and back-gripping means 34 (see FIGS. 2b and 2d). In the joined condition of the two housing parts 4 and 8, the locking or back-gripping means 34 are in a locked condition holding the two housing parts 4,8 together by positive action. Only on activation of the operating element 32, is the lock released so that the housing parts 4, 8 can be separated. By the disposition and constitution of the grip recess 30 and the manually operable element 32 close together and such that a user can grip both in the grip recess 30 and also operate the operating element 32 with one finger of the same hand, a single-hand action for release of the second housing part 8 from the first housing part 4 is implemented. This proves especially advantageous because, in that case, a second housing part 8 filled with body fluids can be released with just one hand and placed in a disposal container.

To join the two housing parts 4, 8, the second housing part 8 is placed at a slight inclination from the rear and upward with its lower edge on two spigots forming a pivot 33 (FIG. 2d) of the first housing part 4. In the second housing part, a recessed region 35 (FIG. 3a) is formed on the lower edge to receive the spigot 33. If spigot 33 and the recessed region 35 are engaged, the second housing part 8 can be pivoted with respect to the first housing part 4. In this way, the sides 18, 20 facing each other are placed one upon the other and thus enter the intended position with self-centering (supported by further guidance or centering means 37, FIGS. 2d, and 39, FIG. 3a, and the complementary shapes of the sides 18, 20 of the housing parts 4,8 facing each other). By moving the two housing parts 4, 8 one against the other, in particular, essentially transversely with respect to the vertical separation plane 14, the locking and back-gripping means 34 is automatically deflected and then latches in the position that locks the housing parts 4, 8 against each other. For this purpose, on the second housing part 8, a latching hook 41 (FIG. 3i) is provided under which the locking or back-gripping means 34 grips. If the housing parts 4, 8 are put in their locked position, vacuum communication is then automatically established between the interior of the vessel 10 of the second housing part 8 and the vacuum-producing device through connection means 36 (described later in connection with FIG. 5).

A visible side 38 of the first housing part 4 facing away from the body is constituted with a slight inclination from the vertical so that the shape of the disk tapers in the upward direction. In this way, the visible side 38 can be more easily seen. Operating elements 40 and display elements 42, in particular, in the form of a touchscreen are provided there. Essentially, the entire visible side 38 is overlapped or constituted by a large-surface cover 44 so that no dirt-trapping joints are formed in the region of the operating elements 40.

Moreover, in the region of the separation plane 14 between the contacting housing parts 4, 8, the figures show a plug slot 46 for plugging and releasably fixing a fastening means, in particular, and preferably in the form of a flexible belt, or a bow or a strap, on which, for example, a belt or a carrying shoulder strap can be fastened, or in another form. It proves advantageous if this fastening means can be separated from the housing parts 4, 8 and is therefore no obstacle if the device 2 is used in stationary operation, that is, standing on a preferably level surface 16, for example, if a patient to be treated with the device 2 is resting in a hospital bed. FIG. 2d indicates, on the side 18 of the first housing part 4, means 48 on which the fastening means plugged into the plug slot 46 are fixed or held.

The further embodiment of the inventive device shown in FIGS. 4a to e differs from the embodiment shown in FIG. 3 in that the second housing part 8 and the vessel 10 constituted by it has a larger volume. The bevel in the upper region of the side 22 of the second housing part 8 facing the body, in which the grip cavity 30 is formed, is somewhat more inclined away from the body of the user. This permits even better access. This larger second housing part 8 is more suitable for stationary operation of the device 2; it could have an outwardly convex side 22 for this purpose or even be formed with a greater protrusion than is shown in FIG. 4.

Figure 5:
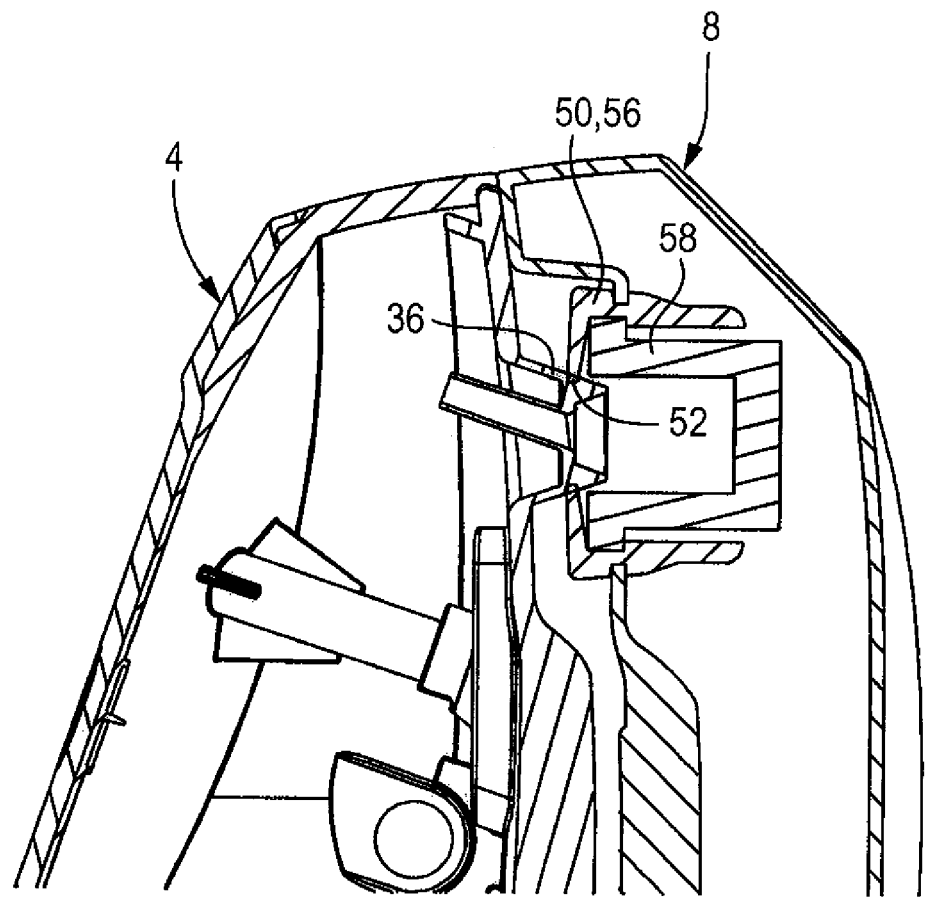
FIG. 5 a sectional view through the device in the region of the vacuum communication between the first and the second housing part.

FIG. 5 shows in detail the nature of the vacuum communication between the interior of the second housing part 8 constituting the vessel 10 and the first housing part 4. The suction side of a vacuum-producing device, not depicted, leads to the conically shaped connection means 36 that tapers conically toward the second housing part 8. In this way, an at least slightly compliant mating connection means 50 of the second housing part 8 that, in the example shown, has a circular opening 52 that is bounded by a compliant sealing lip 54, can be applied with sealing, against the conical connection means 36 of the first housing part 4. This mating connection means 50 exits into the interior of the second housing part 8. It also forms a filter receiving means 56 for a filter 58 that, in the example shown, is constituted as a cup-shaped filter and prevents bacteria from being suctioned into the first housing part 4. It is immediately apparent that, on moving the two housing parts 4, 8 one against the other, the connection means 36 of the first housing part 4 forms a pressure communication sealed outwardly with the mating connection means 50 of the second housing part 8.

The coupling between the connection 13 for a measuring or rinsing duct and the associated also exemplary conically formed connection means 60 on the first housing part 4 is formed in a similar way. As can be seen from FIG. 3g, a coupling or grommet part, not depicted, can be inserted into the passage opening 62 in the second housing part 8 that then forms the connection 13 shown in FIG. 1d for the measuring or rinsing duct. This coupling or grommet part, not depicted, can then be coupled pressure-tight with the conical connection means 60. In this way, a fluid medium, in particular, air or a rinsing liquid can be guided into the wound through a tube to support the removal by suction of wound exudates. A measuring or rinsing tube and the suction tube are typically accessories for the second housing part that are single-use components; they are disposed of together with the second housing part after use.

Finally, FIGS. 6 and 7 illustrate differently sized standing surfaces 64 (with approx. 7 $cm^2$) and 66 (with approx. 55 $cm^2$) with differently sized second housing parts 8 of the embodiments according to FIGS. 1 and 4. The housing parts 8 can be set down on a surface on these standing surfaces 64 or 66 if they are removed from the first housing part 4. If they are held on the first housing part 4, the standing surface of the device 2 is constituted by the first housing part 4. Foot elements can also be provided on the standing surfaces of the housing parts 4, 8, as can be seen from the FIGS. 1b, 2b, 4b.

We claim:

1. An apparatus for carrying on the body of a user to generate a vacuum for medical applications and for vacuum therapy of a wound on a human or animal body, the apparatus comprising:
   a first housing part;
   a second housing part, wherein said second housing part is a vessel for receiving body fluids and for receiving wound exudates suctioned out of the wound, said vessel being disposable after use, said vessel having a gripping opening that passes through said vessel, thereby forming a manual gripping region, wherein said vessel has an outer side wall, an inner side wall, an outer peripheral wall and an inner peripheral wall, said gripping opening passing through said outer and inner side walls and being directly surrounded by said inner peripheral wall, said manual gripping region thereby being defined by contiguous portions of said outer side wall, said inner side wall, said outer peripheral wall and said inner peripheral wall;
   a vacuum-producing device disposed in or on said first housing part;
   a connection communicating with said vessel, said connection structured to receive a suction tube leading to the body for transferring the body fluids to said vessel;
   a fastening mechanism structured such that the apparatus can be worn by and carried on the body of the user;
   a locking or back-gripping mechanism disposed between and communicating with said first and said second housing parts to fix said second housing part to said first housing part in a separable manner through snap-in, latching, or other positive-action; and
   an operating element cooperating with said locking or back-gripping mechanism, wherein said locking or back-gripping mechanism can be moved into a release direction by manual operation of said operating element, wherein said operating element for said locking or back-gripping means is disposed above said gripping opening and proximate to said manual gripping region so that a user or a caregiver can, with only one hand, release said locking or back-gripping means while gripping said second housing part to mutually separate said first and said second housing parts from another, said gripping opening and said locking or back-gripping means being structured and arranged such that the user or caregiver can grip, hold and lift said second housing part through manual engagement of fingers of one hand into said gripping opening while operating said operating element with his or her thumb, so that there is one handed access to said second housing part for unlocking and removal of said second housing part from said first housing part, removal being effected through engagement of fingers of one hand into said gripping opening.

2. The apparatus of claim 1, wherein said gripping opening is disposed in an upper region of said second housing part which is inclined away from the body.

3. The apparatus of claim 2, wherein said manual gripping region is disposed on a side of said second housing part facing the body.

4. The apparatus of claim 1, wherein said locking or back-gripping mechanism projects from a separation plane of one of said first and said second housing parts and can be deflected transversely with respect to the joining direction of said first and said second housing parts during joining thereof for placement into a back-gripping position.

5. The apparatus of claim 1, wherein said manually operable operating element is provided on a top side of the device or as a button that can be pressed in.

6. The apparatus of claim 1, wherein said first housing part faces away from the body when the apparatus is carried on the body of the user during mobile operation thereof and the second housing part faces the body.

7. The apparatus of claim 1, wherein both said first and said second housing parts are disk-shaped and can lie one against an other at a vertically oriented separation plane.

8. The apparatus of claim 1, wherein said second housing part has a concave shape toward the body of the user in at least one plane or in at least one horizontal plane on a side thereof facing the body of the user.

9. The apparatus of claim 8, wherein sections of said concave shape have a radius of curvature of 300-500 mm.

10. The apparatus of claim 1, wherein regions of said second housing part are of concave shape toward the body of the user in a horizontal plane and in a vertical plane on a side thereof facing the body of the user.

11. The apparatus of claim 10, wherein sections of said concave shape have a radius of curvature of 500-900 mm.

12. The apparatus of claim 1, wherein said second housing part on a side facing the body of the user and in a region facing away from a standing side of the apparatus has a bevel facing away from the body of the user towards said first housing part.

13. The apparatus of claim 1, wherein said second housing part is formed with a bevel on a side thereof facing the body in a transition to side walls of said second housing part or to side walls of said first housing part.

14. The apparatus of claim 1, wherein said first and said second housing parts have centering elements on sides thereof facing each other.

15. The apparatus of claim 1, wherein said first and said second housing parts can be joined one against an other, transversely with respect to a separation plane.

16. The apparatus of claim 15, wherein one of said first and said second housing parts can be placed on a contact surface of an other one of said first and said second housing part with an upward inclination with respect to a vertical and can then be pivoted into contact with said other housing part transversely with respect to said separation plane.

17. The apparatus of claim 1, wherein, on joining said first and said second housing parts, vacuum communication is also established between said vessel and said vacuum-producing device.

18. The apparatus of claim 1, wherein a center of gravity of the apparatus is in a lower half thereof.

19. The apparatus of claim 1, wherein a ratio of a standing surface of the apparatus to a height thereof is 4.0-6.0 $cm^2$/cm.

20. The apparatus of claim 1, wherein a standing surface of the apparatus is constituted by said first housing part.

21. The apparatus of claim 1, wherein said first housing part covers said second housing part when viewed onto a visible side of said first housing part facing away from the body, thereby concealing at least 90% of a visible surface in that viewing direction or completely concealing said visible surface.

22. The apparatus of claim 1, further comprising a plurality of second housing parts, each with a vessel, wherein said second housing parts and said vessels have different sizes or have different sizes in a depth direction thereof.

23. The apparatus of claim 1, further comprising a filter disposed between said vessel and said vacuum-producing device, said filter being disposable after use or being disposable together with said vessel.

24. The apparatus of claim 1, further comprising a filling level indicator for said vessel.

25. The apparatus of claim 24, wherein a monitoring facility outputs an alarm depending on a filling level reached in said vessel.

26. The apparatus of claim 24, wherein operating elements and display elements for said vacuum-producing device are provided on a visible side of said first housing part facing away from the body.

27. The apparatus of claim 26, wherein said operating elements are constituted by a touchscreen.

28. The apparatus of claim 1, further comprising an inclination sensor disposed on said first housing part to cause a display on a display element to rotate through 180° at a defined inclination of said first housing part with respect to a vertical by means of a control device so that said display can be read by the user from above.

29. The apparatus of claim 1, wherein a visible side of said first housing part facing away from the body is constituted or overlapped by a large-surface cover so that dirt-trapping joints in a region of said operating elements are avoided.

30. The apparatus of claim 1, wherein said first housing part has an interface for data exchange or a USB interface disposed at a separation plane with respect to said second housing part and is thereby covered and protected against soiling by said second housing part.

31. The apparatus of claim 1, wherein said fastening mechanism comprises a flexible strip-shaped section or a plurality of such sections that can be releasably fastened on opposite sides of said first and/or said second housing part.

32. The apparatus of claim 1, wherein said fastening mechanism is releasably disposed between said first and said second housing parts, lying one against the other or pluggable into a plug slot between said first and said second housing parts, lying one against the other.

33. The apparatus of claim 1, wherein, in a joined condition of the apparatus, said first and said second housing parts do not have any back-grippable components on an outer side, with an exception of said connection for the suction tube or a measuring or rinsing duct and said gripping opening.

\* \* \* \* \*